United States Patent

Hägel et al.

Patent Number: 5,856,586
Date of Patent: Jan. 5, 1999

[54] PROCESS FOR PRODUCING 2,5-DIMETHYL-2,5-DIHYDROPEROXYHEXANE

[75] Inventors: Eberhard Hägel, Icking; Werner Zeiss, Eurasburg, both of Germany

[73] Assignee: Peroxid-Chemie GmbH, Pullach, Germany

[21] Appl. No.: 776,327

[22] PCT Filed: Jul. 27, 1995

[86] PCT No.: PCT/EP95/02987

§ 371 Date: Jan. 24, 1997

§ 102(e) Date: Jan. 24, 1997

[87] PCT Pub. No.: WO96/03372

PCT Pub. Date: Feb. 8, 1996

[30] Foreign Application Priority Data

Jul. 28, 1994 [DE] Germany .............................. 4426839.4

[51] Int. Cl.⁶ ................................................. C07C 409/00
[52] U.S. Cl. ............................................................. 568/571
[58] Field of Search ............................................... 568/571

[56] References Cited

U.S. PATENT DOCUMENTS 2,996,549  8/1961  Mageli .
4,154,768  5/1979  Leveskis .

FOREIGN PATENT DOCUMENTS 0513711  11/1992  European Pat. Off. .
1291965   3/1962  France .
 936008   9/1963  United Kingdom .

OTHER PUBLICATIONS

Chemische Berichte vol. 88, pp. 712–716, Criegee, May 1955.

Mar. "Advanced Organic Chemistry" p. 617, 1968.

Morrison and Boyd "Organic Chemistry" 3rd edition, pp. 166–171, 1975.

Primary Examiner—Paul J. Killos
Assistant Examiner—Jean F Vollano
Attorney, Agent, or Firm—Fulbright & Jaworski, LLP.

[57] ABSTRACT

Disclosed is a process for the preparation of 2,5-dimethyl-2,5-dihydroperoxyhexene by reaction of 2,5-dimethyl-1,5-hexadiene with hydrogen peroxide in an acidic medium. According to this process, the 2,5-dimethyl-2,5-dihydroperoxyhexane can be prepared with good yield and in a technically simple way.

14 Claims, No Drawings

PROCESS FOR PRODUCING 2,5-DIMETHYL-2,5-DIHYDROPEROXYHEXANE

This application is a 371 of PCT/EP95/02985, filed Jul. 27, 1995.

BACKGROUND OF THE INVENTION

The present invention is in a process for the preparation of 2,5-dimethyl-2,5-dihydroperoxyhexane by the reaction of 2,5-dimethyl-1,5-hexadiene with hydrogen peroxide in an acidic medium.

2,5-Dimethyl-2,5-dihydroperoxyhexane (DHHP) is an important starting material for the preparation of cross-linking peroxides (dialkyl peroxides, such as e.g. 2,5-dimethyl-2,5-di-tert.-butylperoxyhexane, or perketals, such as 3,3,6,6,9,9-hexamethyl-1,2,4,5-tetraoxacyclonotane)(cf. GB-PS 936008), as well as of highly reactive bifunctional peresters.

In FR-PA 1291965 discloses the preparation of 2,5-dimethyl-2,5-di-tert.-butylperoxyhexane from 2,5-dimethyl-1,5-hexadiene by reaction with tert.-butylhydroperoxide. However, the yield of 26% thereby obtained is very unsatisfactory and, furthermore, according to this process, only dialkylperoxides but no perketal or perester derivatives of DHHP are obtained.

From the prior art, a process for the preparation of 2,5-dimethyl-2,5dihydroperoxyhexane (DHHP), from 2,5-dimethylhexane with oxygen is known.

EP-A-0513711 describes a process for the preparation of aliphatic hydroperoxides, e.g. of 2,5-dimethyl-2,5dihydroperoxyhexane (DHHP), by the reaction of a corresponding tetrahydrofurane derivative with hydrogen peroxide.

U.S. Pat. No. 4,154,768 describes a general process for the preparation of tert.-alkylhydroperoxides from asymmetric secondary olefins by reaction with hydrogen peroxide in a reaction mixture containing a strong acid.

According to JP-A-3215468 and JP-A-3190856, hydroperoxides are obtained by the reaction of an olefin or alcohol with hydrogen peroxide in the presence of a strong acid.

Usually, the preparation of 2,5-dimethyl-2,5dihydroperoxyhexane (DHHP) takes place by the reaction of 2,5-dimethylhexane-2,5-diol with hydrogen peroxide in the presence of an acidic catalyst, in general using sulphuric acid (cf. Rust, J. Am. Chem. Soc. 79 (1957) 4000, 4002; L. Criegee, Erdöl und Kohle, 15 (1962) 523, 524, 528; Criegee and Paulig, Chem. Ber., 88 (1955), 712, 716; Criegee and Dietrich, Liebigs Ann. Chem. 560 (1948) 141; L. Dulog and A. Sanner, Tetrahedron Letters, 51 (1966) 6353–6358). According to these processes, the dosing of the diol takes place as a solid, which is a disadvantage. Another disadvantage of this process is the easy formation of cyclisation products (e.g. 2,2,5,5-tetramethyltetrahydrofuran) from the diol under the influence of acids which gives poor yields of dihydroperoxide and a contaminated product.

Therefore, there was still a great need for a process for the preparation of 2,5-dimethyl-2,5-dihydroperoxyhexane (DHHP) which can be carried out in a simple and technically advantageous way, and by which the DHHP is obtainable in high yield.

This problem has been solved by the process of the present invention.

THE INVENTION

The subject of the present invention is a process for the preparation of 2,5-dimethyl-2,5-dihydroperoxyhexane (DHHP) according to claim 1 by reaction of 2,5-dimethyl-1,5-hexadiene with hydrogen peroxide in an acidic medium.

At ambient reaction temperatures, almost no reaction takes place between 2,5-dimethyl-1,5-hexadiene and an aqueous mixture of hydrogen peroxide and sulphuric acid. However, after addition of a small amount of a suitable emulsifier or of a solvent which is miscible with water, a rapid reaction to DHHP takes place.

Therefore, the reaction is preferably carried out in an acidic aqueous medium and with addition of an emulsifier or of a water-miscible solvent.

As water-miscible solvent there can be used: triethyl phosphate, tetrahydrofuran, 1,4-dioxane, glycols or glycol ethers, of which triethyl phosphate is especially preferred.

Especially suitable emulsifiers are non-ionic oxyethylates of aliphatic fatty alcohols or oxoalcohols with 10 to 18 carbon-atoms, such as $C_{13}/C_{15}$-oxoalcohols with 8 to 10 mol ethylene oxide; $C_{10}$-oxoalcohol with 6 to 7 mol ethylene oxide; $C_{13}$-oxoalcohol with 8 mol ethylene oxide; $C_{10}/C_{12}$-fatty alcohol propoxylated/ethoxylated and sorbitan ester oxyethylates.

The reaction takes place preferably at a temperature in the range of 0° to 60° C. and especially in the range of 10° to 50° C. However temperatures above or below these temperature ranges are also possible, depending especially upon the reaction medium used and/or the acid used.

As acidic catalyst, an acid is preferably used which is selected from the group consisting of sulphuric acid, phosphoric acid, alkylsulphonic acid, optionally substituted arylsulphonic acids, polyphosphoric acid and perchloric acid, whereby sulphuric acid is especially preferred.

In an especially preferred embodiment of the process according to the invention, the 2,5-dimethyl-1,5-hexadiene is added with stirring to an aqueous mixture of hydrogen peroxide and sulphuric acid and emulsifier.

The hydrogen peroxide concentration in the reaction medium preferably amounts to 20 to 50 wt. % and especially 30 to 50 wt. %. The hydrogen peroxide is preferably used in a molar excess, and especially in a ratio of 1 mol of 2,5-dimethyl-1,5-hexadiene to 3 to 8 mol and especially preferred of 5 mol of hydrogen peroxide.

The obtainable yield of 2,5-dimethyl-2,5-dihydroperoxyhexane (DHHP) by the process according to the invention is very good and, as a rule, amounts to at least 55% (referred to 2,5-dimethyl-1,5-hexadiene). Furthermore, with 2,5-dimethyl-1,5-hexediene, a starting material is used which is a liquid under the process conditions, whereby a technically laborious solid material dosing, as in the case of the process for the preparation of DHHP by reaction of 2,5-dimethylhexane-2,5-diol with hydrogen peroxide, can be avoided.

The following Examples are to explain the present invention in more detail without limiting it thereto.

EXAMPLE 1

113 g (1.0 mole) of 2,5-dimethyl-1,5-hexadiene are added to a mixture of 194 g (4.0 moles) of 70% hydrogen peroxide, 150 g (1.1 moles) of 72% sulphuric acid and 25 g of triethyl phosphate under stirring and cooling within about 50 minutes. The temperature is kept at about 30° C. throughout this procedure. After a few minutes, the DHHP crystallization starts. After complete addition, stirring at 30° C. is continued for 2 hours. The reaction mixture is diluted with 100 ml of water, filtered, and the solid DHHP is washed with cold water. The solid consists of 112.4 g of water-wet DHHP with a content of 80.4% DHHP (corresponding to 50.7% of the theoretical yield).

EXAMPLE 2

226 g (2.0 moles) of 2,5-dimethyl-1,5-hexadiene are added to a mixture of 329 g (8.0 moles) of 70% hydrogen peroxide, 218 g (1.6 moles) of 72% sulphuric acid and 4 g of Tween 21 (sorbitan monolaurate-4 EO) under stirring and cooling, starting at 25° C. The temperature of the mixture is kept at a maximum of 35° C. After a few minutes the DHHP crystallization starts. After complete addition, stirring is continued at 30° C. for 2 hours. The reaction mixture is diluted with 250 ml of water, filtered, and the solid DHHP is washed with cold water until it is free of hydrogen peroxide. The solid consists of 310 g of water-wet DHHP with a content of 73.4% DHHP (corresponding to 63.8% of the theoretical yield).

EXAMPLE 3

Using the same procedure as in Example 2, 170 g (1.5 moles) of 2,5-dimethyl-1,5-hexadiene are added to a mixture of 301 g (6.0 moles) of 68% hydrogen peroxide, 214 g (1.42 moles) of 65% sulphuric acid and 3 g of Lutensol TO 8 ($C_{13}$-oxoalcohol with 8 moles of ethylene oxide). The solid consists of 252 g of water-wet DHHP with a content of 76.2% DHHP (corresponding to 71.8% of the theoretical yield).

EXAMPLE 4

Using the same procedure as in Example 2, 113 g (1.0 mole) of 2,5-dimethyl-1,5-hexadiene are added to a mixture of 315 g (6.3 moles) of 68% hydrogen peroxide, 210 g (1.39 moles) of 65% sulphuric acid and 2 g of Marlox FK 86 E ($C_{10}C_{12}$-fatty alcohol propoxylated/ethoxylated). The solid consists of 182 g of water-wet DHHP with a content of 73.1% DHHP (corresponding to 74.6% of the theoretical yield).

It will be understood that the specification and examples are illustrative but not limitative of the present invention and that other embodiments within the spirit and scope of the inventions will suggest themselves to those skilled in the art.

We claim:

1. A process for the preparation of 2,5-dimethyl-2, 5dihydroperoxyhexane comprising: reacting 2,5-dimethyl-1,5-hexadiene with hydrogen peroxide in an acidic aqueous medium comprising an acidic catalyst and an emulsifier at a temperature of from 0° to 60° C.

2. The process of claim 1 wherein said acidic catalyst is selected from the group consisting of sulphuric acid, phosphoric acid, alkylsulfonic acid, arylsulphonic acid, polyphosphoic acid and perchloric acid.

3. The process of claim 1 wherein said emulsifier is selected from the group consisting of a non-ionic oxyethylate of a fatty alcohol and oxoalcohol with 10 to 18 C-atoms.

4. The process of claim 1 wherein said 2,5-dimethyl-1,5-hexadiene is added to said aqueous medium under stirring, wherein said acidic catalyst is sulphuric acid.

5. The process of claim 9 wherein the reaction is carried out with addition of a water-miscible solvent.

6. The process of claim 5 wherein said water-miscible solvent is triethyl phosphate.

7. The process of claim 1 wherein the temperature is in the range of 10° C. to 50° C.

8. The process of claim 1 wherein said acidic catalyst comprises sulphuric acid.

9. A process for the preparation of 2,5-dimethyl-2,5-dihydroperoxyhexane comprising reacting 2,5-dimethyl-1,5-hexadiene with hydrogen peroxide in an acidic aqueous medium comprising an emulsifier.

10. The process of claim 18 wherein the emulsifier is selected from the group consisting of a non-ionic olyethylate of a fatty alcohol, an oxoalcohol with 10–18 carbon atoms, or mixtures thereof.

11. The process of claim 18 wherein the 2,5-dimethyl-1,5-hexadiene is added to an aqueous mixture of hydrogen peroxide, sulphuric acid and emulsifier while stirring.

12. A process for the preparation of 2,5-dimethyl-1,5-dihydroperoxyhexane comprising reacting 2,5-dimethyl-1,5-hexadiene with hydrogen peroxide in an acidic aqueous medium comprising triethyl phosphate.

13. The process of claim 21 wherein the reaction is performed at a temperature of from 0° to 60° C.

14. The process of claim 19 wherein the reaction is conducted at a temperature of from 0° to 60° C.

* * * * *